(12) United States Patent
Burgess et al.

(10) Patent No.: US 7,846,142 B2
(45) Date of Patent: Dec. 7, 2010

(54) FLUID COLLECTION SYSTEM AND METHODS OF USING SAME

(75) Inventors: James E. Burgess, Long Grove, IL (US); Kenneth S. Chua, Glenview, IL (US); Joseph B. Dunn, Kansasville, WI (US); Dale F. Greeson, Jr., Palatine, IL (US); Jack E. Maze, Long Grove, IL (US); Alberto C. Savage, Buffalo Grove, IL (US); Arlene A. Siavelis, Northbrook, IL (US); Jennifer T. Swartz, Libertyville, IL (US); Earl D. Wilson, Ingleside, IL (US)

(73) Assignee: Medline Industries, Inc., Mundelein, IL (US)

( * ) Notice: Subject to any disclaimer, the term of this patent is extended or adjusted under 35 U.S.C. 154(b) by 74 days.

(21) Appl. No.: 11/634,714

(22) Filed: Dec. 6, 2006

(65) Prior Publication Data
US 2008/0140033 A1    Jun. 12, 2008

(51) Int. Cl.
*A61M 1/00*    (2006.01)
(52) U.S. Cl. ...................... 604/317; 604/540
(58) Field of Classification Search ............... 604/317, 604/320–332, 343, 346–347, 349, 353–357
See application file for complete search history.

(56) References Cited

U.S. PATENT DOCUMENTS

| | | | |
|---|---|---|---|
| 3,090,968 A | 5/1963 | Buono | 4/110 |
| 3,220,434 A | 11/1965 | Garth | 137/374 |
| 3,237,624 A | 3/1966 | Jinkens et al. | 128/275 |
| 3,345,023 A | 10/1967 | Scott et al. | 248/95 |
| 3,529,598 A | 9/1970 | Waldman et al. | |
| 3,534,738 A * | 10/1970 | Huck | 604/325 |
| 3,537,109 A | 11/1970 | Spurrier et al. | 4/110 |
| 4,015,605 A | 4/1977 | McWhorter | 128/294 |
| 4,019,707 A | 4/1977 | Quinn et al. | 248/95 |
| 4,027,842 A | 6/1977 | Mittleman | 248/75 |
| 4,051,578 A | 10/1977 | Manschot et al. | 251/4 |
| 4,188,989 A | 2/1980 | Andersen | 150/9 |
| 4,219,177 A | 8/1980 | O'Day | 248/215 |
| 4,305,405 A | 12/1981 | Meisch | 128/762 |
| 4,312,352 A | 1/1982 | Meisch et al. | 128/294 |
| 4,317,550 A | 3/1982 | Hannah | 248/95 |
| 4,393,880 A | 7/1983 | Taylor | 128/760 |
| 4,501,584 A | 2/1985 | Cianci et al. | 604/322 |
| 4,559,937 A | 12/1985 | Vinson | 128/132 |
| 4,562,984 A | 1/1986 | Sherlock et al. | 248/95 |
| 4,650,478 A | 3/1987 | Dunn | 604/322 |
| 4,772,278 A | 9/1988 | Baber | |
| 4,857,042 A | 8/1989 | Schneider | 604/4 |
| 4,886,510 A | 12/1989 | Matsuura | 604/353 |

(Continued)

FOREIGN PATENT DOCUMENTS

WO    99/23978    *    5/1999

*Primary Examiner*—Michele Kidwell
(74) *Attorney, Agent, or Firm*—Nixon Peabody LLP

(57) ABSTRACT

According to one aspect, a fluid collection bag comprises an inlet opening adapted to receive an inlet tube located on a first side of the fluid collection bag. The first side of the fluid collection bag is generally parallel with a length of the fluid collection bag. The fluid collection bag further comprises an outlet opening located on the first side of the fluid collection bag.

20 Claims, 2 Drawing Sheets

U.S. PATENT DOCUMENTS

| | | | |
|---|---|---|---|
| 4,893,587 A | 1/1990 | Bailey, Jr. | 119/95 |
| 5,009,236 A | 4/1991 | Brothers | 128/761 |
| 5,119,675 A | 6/1992 | Mohiuddin | 73/223 |
| 5,148,940 A | 9/1992 | Mendise | 220/404 |
| 5,217,443 A | 6/1993 | Oxley | 604/317 |
| 5,267,989 A | 12/1993 | Moyet-Ortiz | 604/349 |
| 5,356,398 A | 10/1994 | Willis | 604/321 |
| 5,375,799 A | 12/1994 | Rhodes | 248/95 |
| 5,429,624 A | 7/1995 | Coelho, Jr. | 604/323 |
| 5,647,670 A | 7/1997 | Iscovich | 383/33 |
| 5,842,233 A | 12/1998 | Brodén | 4/144.1 |
| 5,911,786 A | 6/1999 | Nielsen et al. | 73/427 |
| 5,935,115 A | 8/1999 | Espina | 604/277 |
| 5,967,200 A | 10/1999 | Hall | 141/86 |
| 6,007,521 A | 12/1999 | Bidwell et al. | 604/264 |
| 6,098,210 A | 8/2000 | Broden | 4/144.1 |
| 6,132,407 A | 10/2000 | Genese et al. | 604/327 |
| 6,212,698 B1 | 4/2001 | Stingley et al. | 4/315 |
| 6,318,419 B1 | 11/2001 | Lee | 141/108 |
| 6,471,680 B1 | 10/2002 | Cawood | 604/327 |
| 6,482,190 B1 | 11/2002 | Genese et al. | 604/327 |
| 6,491,673 B1 | 12/2002 | Palumbo et al. | 604/317 |
| 6,543,064 B1 | 4/2003 | Prall et al. | 4/144.1 |
| 6,716,200 B2 | 4/2004 | Bracken et al. | 604/265 |
| 6,736,803 B2 | 5/2004 | Cawood | 604/327 |
| 6,796,974 B2 | 9/2004 | Palumbo et al. | 604/355 |
| 6,857,137 B2 | 2/2005 | Otto | 4/144.1 |
| 6,858,021 B2 | 2/2005 | Washington | 604/265 |
| 6,887,230 B2 | 5/2005 | Kubalak et al. | 604/544 |
| 6,904,621 B2 | 6/2005 | Otto et al. | 4/144.1 |
| 7,001,370 B2 | 2/2006 | Kubalak et al. | 604/544 |
| 7,008,407 B1 | 3/2006 | Kamp | 604/327 |
| 2007/0203463 A1 | 8/2007 | Salvadori et al. | 604/323 |
| 2007/0203464 A1 | 8/2007 | Green et al. | 604/323 |

* cited by examiner

FLUID COLLECTION SYSTEM AND METHODS OF USING SAME

FIELD OF THE INVENTION

This invention relates to the collecting and measuring of body fluid. More specifically, the present invention is directed to a sanitary fluid collection system and methods of using such a system.

BACKGROUND OF THE INVENTION

Fluid collection systems are typically used in hospitals to monitor the discharge of urine, blood, or exudate from bedridden patients. Such fluid collection systems include a fluid collection bag. The catheter is typically connected to the fluid collection bag and is generally suspended at a patient's bedside. Fluid collection bags generally have an inlet tube near the uppermost portion of the bag where the urine enters and an outlet near the bottom portion of the fluid collection bag, which permits discharge of the urine.

Medical beds that raise and lower are commonly used in healthcare facilities. Placing medical beds in a low position is recommended for patient safety. Having medical beds in a low position makes it easier to tend to patients and provides for a shorter fall should a patient fall from the bed. However, many fluid collection bags rest on the floor when medical beds are in their low position. Since the outlet is typically located at the bottom portion of fluid collection bags, there exists the potential for contamination and the spread of bacteria when fluid collection bags are permitted to rest on the floor.

Accordingly, there exists a need to provide a fluid collection system having a fluid collection bag that is adapted to suspend from a medical bed in a low position without contacting the floor. It would, thus, be desirable to have a fluid collection system having a fluid collection bag that addresses this need.

SUMMARY OF THE INVENTION

According to one aspect of the present invention, a fluid collection bag comprises an inlet opening adapted to receive an inlet tube located on a first side of the fluid collection bag. The first side of the fluid collection bag is generally parallel with a length of the fluid collection bag. The fluid collection bag further comprises an outlet opening located on the first side of the fluid collection bag.

According to another aspect of the present invention, a fluid collection system comprises a fluid collection bag having an inlet opening adapted to receive an inlet tube located on a first side of the fluid collection bag. The fluid collection bag also includes an outlet opening located on the first side of the fluid collection bag and at least one side opening located at or near the first side of the fluid collection bag. The first side of the fluid collection bag is generally parallel with a length of the fluid collection bag. The fluid collection system further comprises a mounting bracket including a base having a base length and a base width. The base has at least one attachment member adapted to removably associate with the at least one side opening of the fluid collection bag.

According to yet another aspect of the present invention, a method of securing a fluid collection bag to an object comprises the act of orienting a longitudinal axis of the fluid collection bag substantially parallel to the ground. The fluid collection bag includes an inlet opening adapted to receive an inlet tube and an outlet opening along a first side of the fluid collection bag. The first side of the fluid collection bag is opposite the ground. The method further comprises the act of removably associating the fluid collection bag with at least one attachment member.

BRIEF DESCRIPTION OF THE DRAWINGS

The foregoing and other advantages of the invention will become apparent upon reading the following detailed description and upon reference to the drawings.

Figure 1:
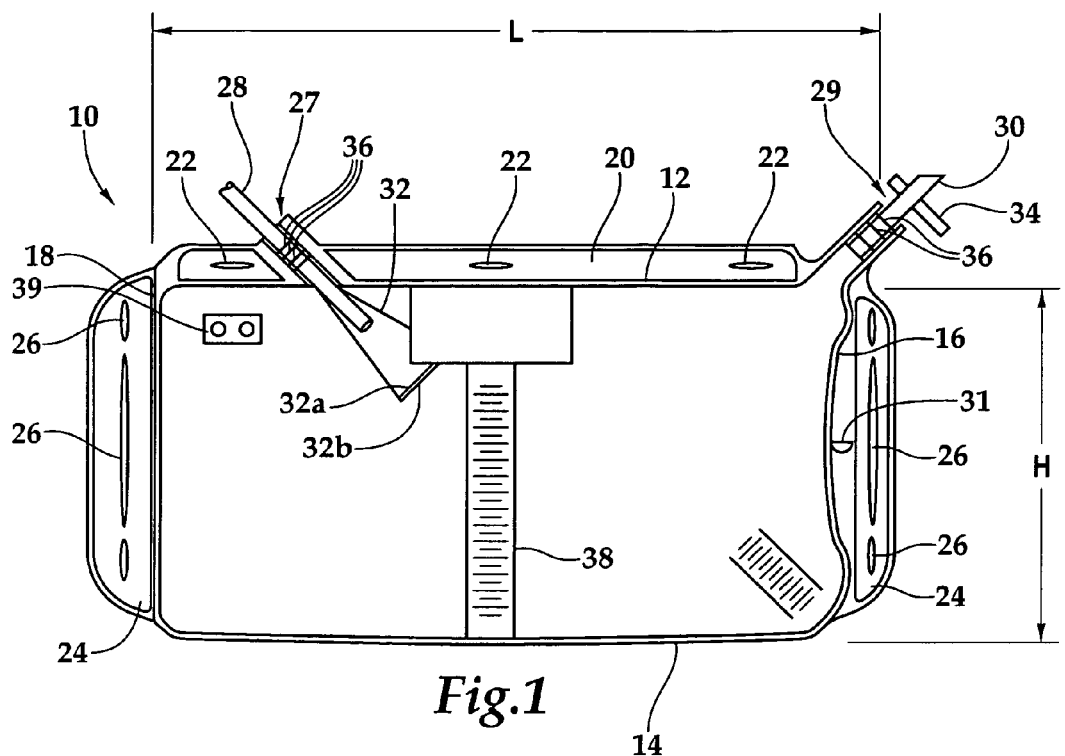
FIG. 1 illustrates a fluid collection bag according to one embodiment.

While this invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

The phrases "fluid collection bag" and "fluid collection system" are used throughout the description and will, thus, be defined for clarity purposes. A "fluid collection bag" is a receptacle for collecting bodily fluid, such as urine, blood, and exudate. A "fluid collection system" includes a receptacle, tubing, connectors, and mechanical supports and may include a means to prevent the backflow of fluid.

Referring initially to FIG. 1, a fluid collection bag 10 adapted for use in a fluid collection system 70 (shown in FIG. 3) is illustrated. The fluid collection bag 10 is generally comprised of plastic. However, the fluid collection bag 10 may be comprised of any impervious flexible or rigid material. The fluid collection bag 10 has a first side 12 and a second side 14 along a length L of the fluid collection bag 10. The fluid collection bag 10 further includes a first end 16 and a second end 18 along a height H of the fluid collection bag 10. The length L of the fluid collection bag 10 is generally greater than the height H of the fluid collection bag 10. In other words, the fluid collection bag 10 has a longitudinal axis LA (illustrated in FIG. 3) aligned with the length L of the fluid collection bag 10. In one embodiment, the length L of the fluid collection bag 10 is approximately twice as long as the height H of the fluid collection bag 10. In other embodiments, the fluid collection bag 10 may have a length L ranging from 1.5 to 5 times the height H of the fluid collection bag 10. However, other dimensional proportions are contemplated and may be used in accordance with one or more embodiments of the present invention. Despite the potential variation in length and height proportions, an elongated length and a shorter height assist in enabling the fluid collection bag 10 to hang on a bed frame and not contact the ground when the bed is in a low position. Thus, the elongated length and shorter height assist in inhibiting the potential for contamination and/or spread of infection. While the fluid collection bag 10 is shown having a generally rectangular shape, the fluid collection bag 10 may take other polygonal and non-polygonal forms.

The first side 12 includes a side reinforcement 20 having one or more side openings 22. The side reinforcement 20 and side openings 22 are adapted to enable the fluid collection bag 10 to be attached to a mounting bracket 50 (see FIG. 2) or other mounting device, as will be described below. Although three side openings 22 are depicted in the embodiment of FIG. 1, any number of side openings 22 suitable for assisting in mounting or otherwise affixing the fluid collection bag 10 onto a mounting bracket 50 or other mounting device may be used. The side reinforcement 20 is generally comprised of plastic. However, other materials may be used for the side reinforcement 20, such as woven or non-woven material, molded or stamped material, wood, metal, paperboard, or any rigid or flexible material. The side openings 22 may be generally elliptically-shaped and should be of a size sufficient to facilitate affixing, mounting, hanging or manipulating the fluid collection bag 10. The side openings 22 may take other shapes than those depicted in the FIGS. The side openings 22 are generally reinforced for ease of use and durability.

The first end 16 and the second end 18 include end reinforcements 24 having one or more end openings 26. The end openings 26 assist in enabling the fluid collection bag 10 to be handled by a nurse or other handler of the fluid collection bag 10. Additionally, the end openings 26 assist in permitting the fluid collection bag 10 to become associated with and/or affixed to other types of objects (see, e.g., FIG. 4). By providing one or more side openings 22 and one or more end openings 26 at different locations on the fluid collection bag 10, the fluid collection bag 10 may be secured to various types of objects including, but not limited to, a bed such as a medical bed, patient aids such as a pole, a chair, a wheelchair, a walker, and a person. The end reinforcements 24 are generally comprised of plastic but can be comprised of woven or non-woven material, molded or stamped material, wood, metal, paperboard, or any rigid or flexible material, as well. The end openings 26 may be generally elliptically-shaped, but may also take other shapes. Furthermore, the end openings 26 are of a size sufficient to facilitate affixing, mounting, hanging or manipulating the fluid collection bag 10. The end openings 26 are generally reinforced for ease of use and durability. Although a total of six end openings 26 are depicted in the embodiment of FIG. 1, any number of end openings 26 suitable for assisting in affixing, mounting, hanging or manipulating the fluid collection bag 10 onto an object may be used. It should be noted that the side openings 22 on the side reinforcements 20 and the end openings 26 on the end reinforcements 24 are generally symmetrical, thereby enabling the fluid collection bag 10 to be affixed, mounted, hung or manipulated to any side of a bed or other object.

An inlet opening 27, adapted to receive an inlet tube 28, and an outlet opening 29 having an outlet tube 30, are located along the first side 12 of the fluid collection bag 10. However, it is contemplated that the fluid collection bag 10 may have additional inlet and outlet openings and tubes. Additionally, the inlet and outlet openings 27, 29 may be located in other positions on the fluid collection bag 12 than those illustrated in the FIGS. Before use of the fluid collection bag 10, the inlet tube 28 is associated with the fluid collection bag 10 at the inlet opening 27 at one end. The exposed end of the inlet tube 28 is typically connected to a catheter (not illustrated). The outlet tube 30 is associated with the fluid collection bag 10 at the outlet opening 29 at one end. The exposed end of the outlet tube 30 may be inserted into a drain tube holder 31.

In the illustrated embodiment, the inlet tube 28 associates with the fluid collection bag 10 at an angle to reduce twisting and to allow for good drainage. In one embodiment, the inlet tube 28 may associate with the fluid collection bag 10 at an angle within the range of about 30° to about 50°. However, it is contemplated that any angle which is suitable for reducing twisting and allowing good drainage for the inlet tube 28 may be used.

Near the inlet opening 27 and internal to the fluid collection bag 10 is an anti-reflux mechanism 32. The anti-reflux mechanism 32 is adapted to generally surround the inlet tube 28 and comprises two sheets 32a, 32b having different lengths in the embodiment shown in FIG. 1. The anti-reflux mechanism 32 may be comprised of vinyl; however, other materials are contemplated for use. Some non-limiting examples of materials for use in the anti-reflux mechanism 32 include plastic film, molded plastic, and rubber. At one end, the anti-reflux mechanism 32 may be associated with the fluid collection bag 10 at or near the inlet opening 27 or the inlet tube 28 itself. The other end of the anti-reflux mechanism 32a, 32b is free. The anti-reflux mechanism 32 assists in allowing fluid to enter the fluid collection bag 10 while inhibiting fluid from exiting the fluid collection bag 10 through the inlet tube 28. To inhibit fluid from exiting through the inlet tube 28, the sheets 32a, 32b collapse and assist in sealing the end of the inlet tube 28 internal to the fluid collection bag 10 when fluid attempts to exit through the inlet tube 28. It should be noted that other types of anti-reflux mechanisms having different designs and/or different numbers of sheets may also be used.

A user may control the exit of fluid from the fluid collection bag 10 through the outlet tube 30 using a valve 34. The valve 34 may be any of those types of valves adapted to open or close a fluid path to allow fluid to drain or keep fluid from draining. In one embodiment, the valve 34 is adapted to replace a drainage hole with a post when activated. In other embodiments, the valve 34 may, for example, be a twist valve, a tube that closes with a mechanical compression against it, or a roller clamp. Additionally, in some embodiments, more than one valve may be utilized.

The inlet tube 28 and the outlet tube 30 may include one or more ribs 36 to discourage kinking or compression within the inlet and outlet tubes 28, 30. The ribs 36 enable good flow through the inlet and outlet tubes 28, 30 and allow for good drainage of the fluid collection bag 10. The fluid collection bag 10 may also include a vent 39 and a printed window 38. The vent 39 is a hydrophilic air vent allowing air transfer to inhibit a vacuum effect on the fluid collection bag 10. The printed window 38 has measurement line(s) to enable easy urine volume output determination.

Figure 2:
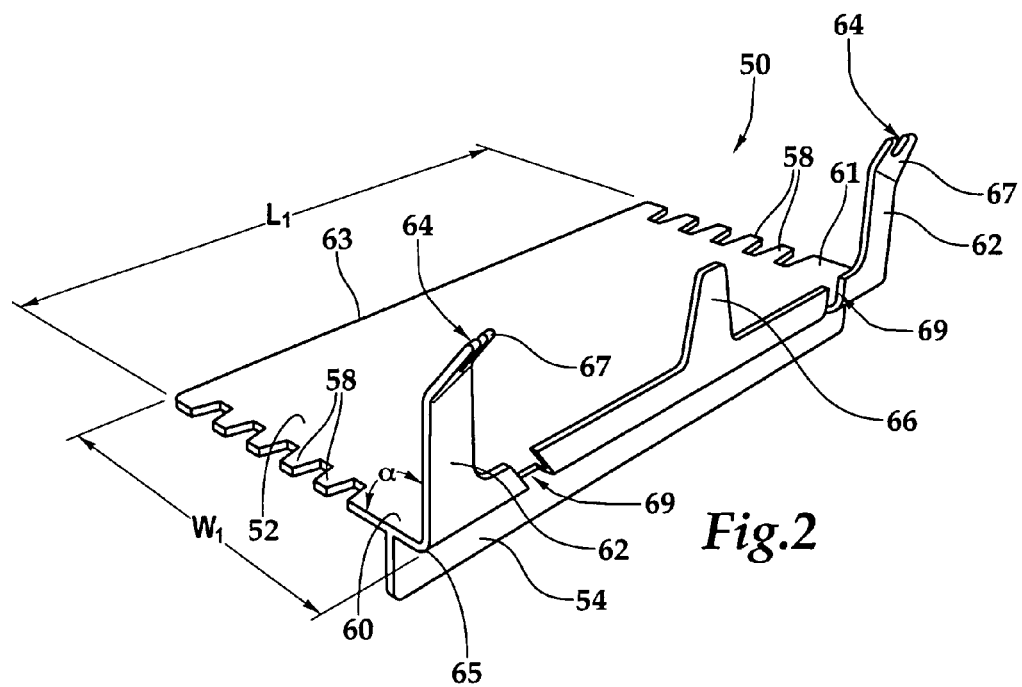
FIG. 2 illustrates a mounting bracket adapted for use with the fluid collection bag of FIG. 1.

Referring now to FIG. 2, the mounting bracket 50 is illustrated according to one embodiment of the present concepts. The mounting bracket 50 is generally comprised of a rigid material for stability. Some non-limiting materials that may be used for the mounting bracket 50 include plastic, wood, metal, or paper board. The mounting bracket 50 may include a base 52 and optionally one or more support members 54. The base 52 has a first end 60 and a second end 61 along a base width $W_1$ of the mounting bracket 50. The base 52 further includes a first side 65 and a second side 63 along a base length $L_1$ of the mounting bracket 50. The base width $W_1$ may be about one-half of an inch (about 1.27 centimeters) or more. In one embodiment, the base width $W_1$ is about six inches (about 15.24 centimeters). In one embodiment, the base length $L_1$ is about ten inches (about 25.4 centimeters). However, other sizes are also contemplated and the base length $L_1$ may be any length sufficient to support the fluid collection bag 10. The support member 54 extends from the base 52 at about the first side 65 of the base 52 in a generally perpendicular direction opposite to attachment members 62. While the mounting bracket 50 is depicted in FIG. 2 as having a generally rectangular shape, it is contemplated that other shapes may be used. It is contemplated that the mounting bracket 50 may take on any configuration or size that is suitable for mounting or otherwise affixing the fluid collection bag 10 onto a bed frame or other desired object.

Generally, the mounting bracket 50 is adapted to removably associate with an object, such as a bed for example. More specifically, the base 52 and the support member 54 of the mounting bracket 50 are adapted to contact an end of a bed frame, wherein the base 52 rests on top of the bed frame and the support member 54 may contact the side of the bed frame (see, e.g., FIG. 3). Although a generally rectangular shape is shown, the shape of the base 52 and support member 54 may vary to enable a removable attachment to different types of objects and different desired end uses. Furthermore, the mounting bracket 50 may include components other than or in addition to the base 52 and support member 54 to associate with desired objects. To enhance the attachment of the mounting bracket 50 to certain objects, the base 52 may include one or more securement tabs 58 located along the first end 60 and/or the second end 61 of the base 52. The securement tabs 58 will be described in further detail below.

As mentioned above, the fluid collection bag 10 is adapted to associate with a mounting bracket such as the mounting bracket 50 depicted in FIG. 2 or with any other mounting device. The mounting bracket 50 may include one or more attachment members 62 adapted to associate with the one or more side openings 22 of the fluid collection bag 10. Although the mounting bracket 50 is shown with two attachment members in FIG. 2, any number of attachment member(s) suitable for mounting or otherwise affixing the mounting bracket 50 or other mounting device to the fluid collection bag 10 may be used. The attachment members 62 form an angle α with the base 52 of the mounting bracket 50. In some embodiments, such as that shown in FIG. 2, the angle α is about ninety-degrees. In other embodiments, the angle α may be greater than 90° (i.e., an obtuse angle). Having an angle α greater than 90° allows the fluid collection bag 10 to hang away from the bed and allow room for fluid to expand the fluid collection bag 10. In some embodiments, the angle α is between about 90° and about 110°.

The attachment members 62 include a top portion 67 having an inlet tube guide 64. The inlet tube guide 64 on the top portion 67 is adapted to receive and hold the inlet tube 28 in place when the fluid collection bag 10 is associated with the mounting bracket 50. The top portion 67 is angled and assists in providing good placement of the inlet tube 28 for good drainage. In the embodiment depicted in FIG. 2, the inlet tube guide 64 is provided on both attachment members 62 because the mounting bracket 50 is "reversible" and may be used on either side of a bed or object. However, in other embodiments, only one of the attachment members 62 may include an inlet tube guide 64. The mounting bracket 50 may optionally include one or more center attachment members 66 to provide additional support for the fluid collection bag 10. The center attachment member 66 may be adapted to associate with one or more side openings 22 of the fluid collection bag 10.

In some embodiments, the mounting bracket 50 may include one or more cut-out portions 69 adapted to receive the inlet opening 27 and inlet tube 28 of the fluid collection bag 10 to facilitate flush mounting of the fluid collection bag 10. The mounting bracket 50 is not limited to comprising one continuous piece. To facilitate storage, shipping, and handling of the mounting bracket 50, the mounting bracket 50 may comprise a plurality of pieces adapted for assembly.

Figure 3:
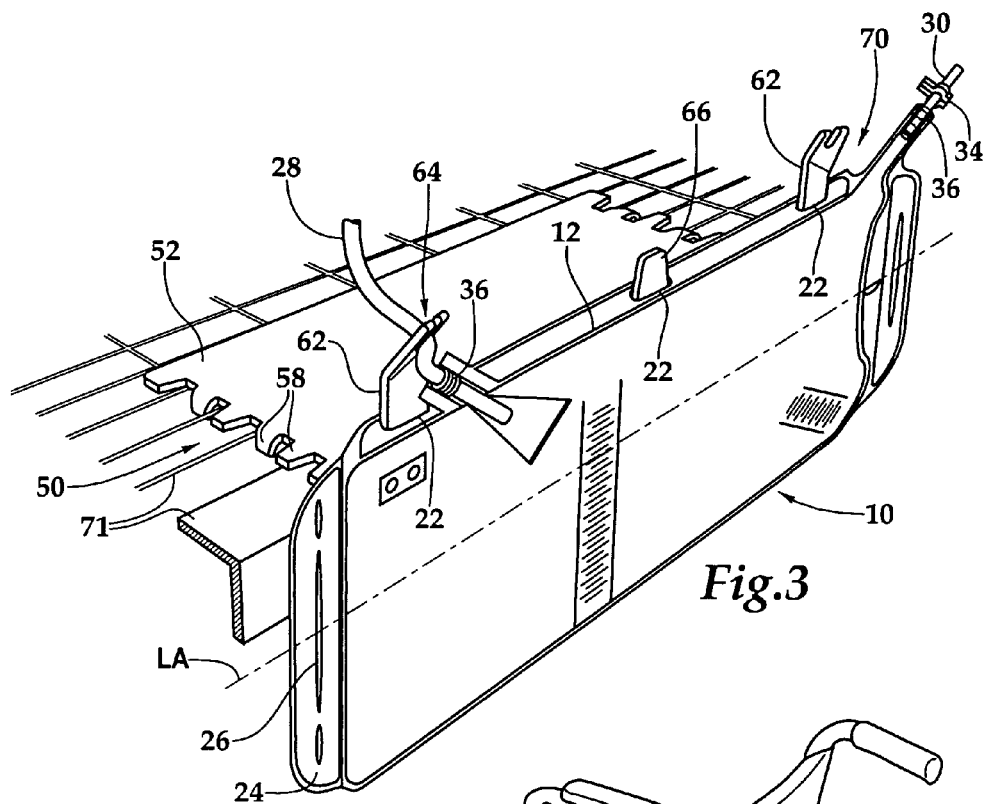
FIG. 3 shows a fluid collection system according to one embodiment shown associated with a bed frame.

Referring now to FIG. 3, the fluid collection system 70, including the fluid collection bag 10 and the mounting bracket 50, are illustrated in use. The base 52 and support member 54 (not visible) of the mounting bracket 50 contact a bed frame 71. The side openings 22 of the fluid collection bag 10 have been placed over the attachment members 62 and center attachment member 66 to provide a removable attachment between the fluid collection bag 10 and the mounting bracket 50. The securement tabs 58 have been bent by a user around portions of the bed frame 71 to further secure the mounting bracket 50 to the bed frame 71. The inlet tube guide 64 maintains the inlet tube 28 in an optimal position for fluid flow through the inlet tube 28.

As illustrated, the longitudinal axis LA of the fluid collection bag 10 is oriented substantially parallel to the ground. Having the outlet tube 30 associated with the fluid collection bag 10 at or near the first side 12 of the fluid collection bag 10 keeps the outlet tube 30 away from the ground. Thus, when a bed is in a low position, the fluid collection bag 10 does not contact or makes minimal contact with the ground and the outlet tube 30 remains away from the ground, inhibiting the potential for contamination and/or spread of infection.

Figure 4:
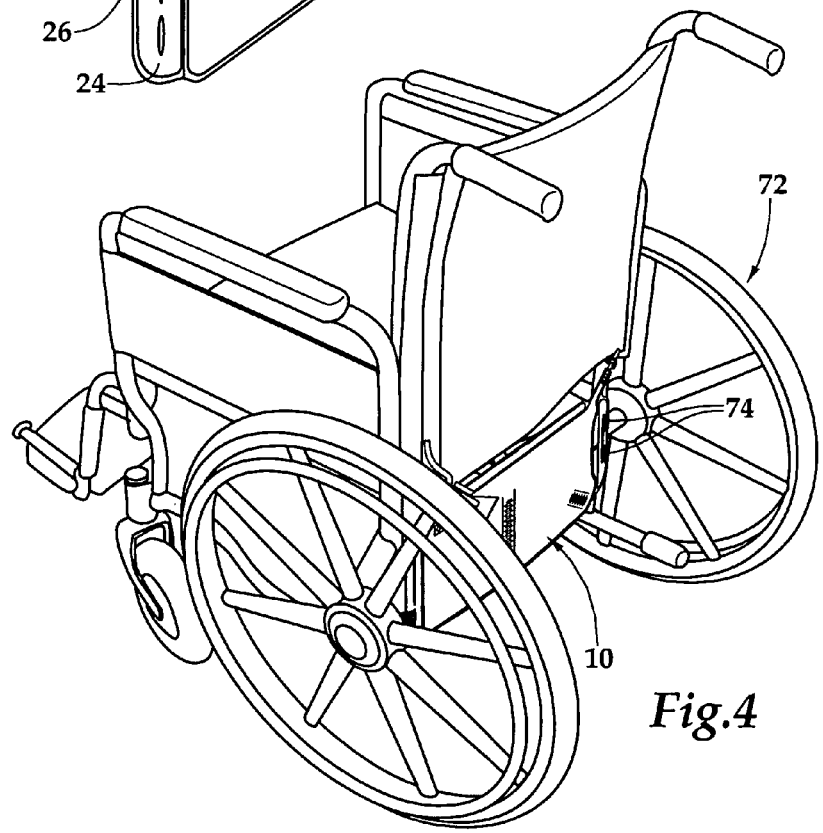
FIG. 4 shows the fluid collection bag according to one embodiment shown associated with a wheelchair.

As mentioned above, the end openings 26 on the end reinforcements 24 are provided to enable attachment of the fluid collection bag 10 to objects in addition to beds. Such additional objects include, but are not limited to, patient aids such as a pole, a chair, a wheelchair, a walker, and person. Referring now to FIG. 4, the fluid collection bag 10 is shown associated with a wheelchair 72. As shown in FIG. 4, one or more pieces of securement material tape 74 may be used instead of or in addition to the mounting bracket 50 to affix the fluid collection bag 10 to a wheelchair or other objects. In one embodiment, the securement material 74 is Velcro® or other hook and loop type fastening devices. In other embodiments, the securement material for affixing, mounting, hanging or otherwise manipulating the fluid collection bag 10 onto the desired object may include snaps, cords, buttons, or other fastening devices.

To use the fluid collection system 70, a user would associate the mounting bracket 50 with an object, such as a bed frame, as illustrated in FIG. 3. The user would then orient the longitudinal axis LA of the fluid collection bag 10 substantially parallel to the ground and removably associate the fluid collection bag 10 with at least one attachment member 62 or 66 of the mounting bracket 50. As illustrated in FIG. 3, the side openings 22 may be utilized to associate the fluid collection bag with the attachment members 62 and 66.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention, which is set forth in the following claims.

What is claimed is:

1. A fluid collection bag made from a fluid impervious material, the fluid collection bag comprising:

an inlet opening formed from the fluid impervious material, the inlet opening being adapted to receive an inlet tube located along an upper peripheral edge of the fluid collection bag at or adjacent to a first lateral end of the fluid collection bag; and an outlet opening formed from the fluid impervious material, the outlet opening being located along the upper peripheral edge of the fluid collection bag at or adjacent to a second opposing lateral end of the fluid collection bag, the outlet opening being separate from the inlet opening, the fluid collection bag having a length that is generally perpendicular to a height of the fluid collection bag, the length being greater than the height of the fluid collection bag, the upper peripheral edge being generally parallel to the length of the fluid collection bag.

2. The fluid collection bag of claim 1, further comprising at least one side opening at or near the upper peripheral edge of the fluid collection bag.

3. The fluid collection bag of claim 1, wherein the length of the fluid collection bag is about twice as long as the height of the fluid collection bag.

4. The fluid collection bag of claim 1, wherein the inlet opening is adapted to receive the inlet tube oriented at an angle within a range of about 30 degrees to about 50 degrees with respect to the upper peripheral edge of the fluid collection bag.

5. The fluid collection bag of claim 1, further comprising an anti-reflux mechanism at or near the inlet opening.

6. The fluid collection bag of claim 5, wherein the anti-reflux mechanism includes at least two sheets having different lengths, the at least two sheets being adapted to surround the inlet tube after the inlet opening has received the inlet tube.

7. The fluid collection bag of claim 6, wherein the at least two sheets are comprised of flexible plastic.

8. A fluid collection system, comprising:
a fluid collection bag made from a fluid impervious material, the fluid collection bag having an inlet opening adapted to receive an inlet tube located on a first side of the fluid collection bag, an outlet opening located on the first side of the fluid collection bag, and at least one side opening located at or near the first side of the fluid collection bag, the first side being generally parallel with a length of the fluid collection bag, the fluid collection bag having a height generally perpendicular to the length of the fluid collection bag, the length being greater than the height of the fluid collection bag, the outlet opening in the fluid collection bag being spaced from the inlet opening in the fluid collection bag such that a portion of the fluid impervious material is located between the inlet opening and the outlet opening; and
a mounting bracket including a base having a base length and a base width, the base length generally corresponds to the length of the fluid collection bag, the base having at least one attachment member adapted to removably associate with the at least one side opening of the fluid collection bag.

9. The fluid collection system of claim 8, wherein the attachment member extends from a first side of the base forming an angle between the base and the attachment member, the first side of the base being generally located along the base length.

10. The fluid collection system of claim 9, wherein the angle is an obtuse angle.

11. The fluid collection system of claim 9, wherein the angle is a right angle.

12. The fluid collection system of claim 9, wherein the at least one attachment member includes an inlet tube guide.

13. The fluid collection system of claim 9, wherein the mounting bracket further includes a support member at or near the first side of the base, the support member being integral with the base, the support member extending from the base in a generally perpendicular direction opposite the attachment member, a support angle being formed between the base and the support member.

14. The fluid collection system of claim 13, wherein the mounting bracket further includes at least one securement tab adapted to secure the mounting bracket to an object, the at least one securement tab being located along at least one of a first end and a second end of the base, the first end and second end being generally perpendicular to the first side of the base.

15. The fluid collection bag of claim 1, wherein the inlet opening is adapted to receive an inlet tube for transporting fluid into the fluid collection bag and the outlet opening is adapted to receive an outlet tube for transporting fluid out of the fluid collection bag.

16. The fluid collection system of claim 8, wherein the inlet opening is adapted to receive an inlet tube for transporting fluid into the fluid collection bag and the outlet opening is adapted to receive an outlet tube for transporting fluid out of the fluid collection bag.

17. The fluid collection bag of claim 1, wherein the fluid collection bag has a generally rectangular shape.

18. A fluid collection system, comprising:
a generally rectangular fluid collection bag made from a fluid impervious material, the fluid collection bag having a length that is generally perpendicular to a height of the fluid collection bag, the length being greater than the height of the fluid collection bag, the fluid collection bag including:
an inlet opening formed from the fluid impervious material, the inlet opening being adapted to receive an inlet tube located along an upper peripheral edge of the fluid collection bag at or adjacent to a first lateral end of the fluid collection bag, the upper peripheral edge being generally parallel to the length of the fluid collection bag, the inlet tube being adapted to transport fluid into the fluid collection bag;
an outlet opening formed from the fluid impervious material, the outlet opening being located along the upper peripheral edge of the fluid collection bag at or adjacent to a second opposing lateral end of the fluid collection bag, and the outlet tube being adapted to transport fluid out of the fluid collection bag, the outlet opening being separate from the inlet opening;
at least one side opening located at or near the upper peripheral edge of the fluid collection bag; and
a mounting bracket including:
a base having a base length and a base width, the base length generally corresponds to the length of the fluid collection bag;
at least one attachment member extending from the base, the at least one attachment member adapted to removably associate with the at least one side opening of the fluid collection bag;
an inlet tube guide integral with a portion of the at least one attachment member that extends through the at least one side opening when the at least one attachment member is removably associated with the at least one side opening.

19. The fluid collection system of claim 18, wherein the inlet opening and the outlet opening are not provided through a common lead-in in the fluid impervious material.

20. The fluid collection system of claim 18, wherein the inlet opening forms an acute angle with the upper peripheral edge and the outlet opening forms an obtuse angle with the upper peripheral edge.

* * * * *